US00PP10881P

United States Patent [19]

Roberson

[11] Patent Number: Plant 10,881

[45] Date of Patent: May 4, 1999

[54] HEMEROCALLIS PLANT 'ROBGLOPER'

[76] Inventor: Robert J. Roberson, 31706 E. Pink Hill Rd., Grain Valley, Jackson County, Mo. 64029

[21] Appl. No.: 08/841,309

[22] Filed: Apr. 30, 1997

[51] Int. Cl.[6] ..... A01H 5/00

[52] U.S. Cl. ..... Plt./312

[58] Field of Search ..... Plt./87.4, 312

*Primary Examiner*—Howard J. Locker
*Assistant Examiner*—Kent L. Bell
*Attorney, Agent, or Firm*—Rothwell, Figg, Ernst & Kurz

[57] ABSTRACT

A new variety of Hemerocallis daylily distinguished by its bloom beauty in both clarity of peach color and round, ruffled form particularly characterized by its strong short scape, thick heavy bloom substance, bloom fragrance and its reblooming habit.

1 Drawing Sheet

SUMMARY OF THE INVENTION

A new variety of daylily distinguished by its bloom beauty in both clarity of peach color and round, ruffled form, particularly characterized by its strong short scape, thick heavy bloom substance, bloom fragrance and its reblooming habit.

BACKGROUND OF THE INVENTION

This new variety of daylily plant originated as a seedling selected from a group of seedlings planted by me at my ranch in Grain Valley, Mo., and resulting from a crossing of the clonal cultivar 'Martha Adams' (unpatented) with the variety Seedling No. RJR-PK3-89, the objective being to produce a plant having blooms of clear peach color borne on a scape height of about 20 to 22 inches. A further objective was to produce such a plant that would be repeat blooming, fragrant, and have blooms with heavy substance and sun resistance.

This new plant was elected for propagation because it most closely possessed the advantageous features that I sought and asexual reproduction of the selected plant was accomplished by division at the crown or basal plate which is the area where the roots and foliage meet, at Grain Valley, Mo.

During the course of propagation of this new plant on a more-or-less commercial scale at my daylily ranch in Grain Valley, Mo., I have observed that the new plant is very hardy when grown in zone 6–9 and its particularly capable of consistently beautiful blooms, on strong, short scapes.

The clumps should be divided or separated every 3 to 5 years depending on the USDA zone and the increase rate. This separation is to maintain optimum continued growth and bloom beauty. The specimens will continue to flower for many years without division although the quality of performance will be diminished. Furthermore, I have observed that the new plant has bloom fragrance, heavy bloom substance, and has a repeat blooming habit.

DESCRIPTION OF THE NEW PLANT

Figure 1:
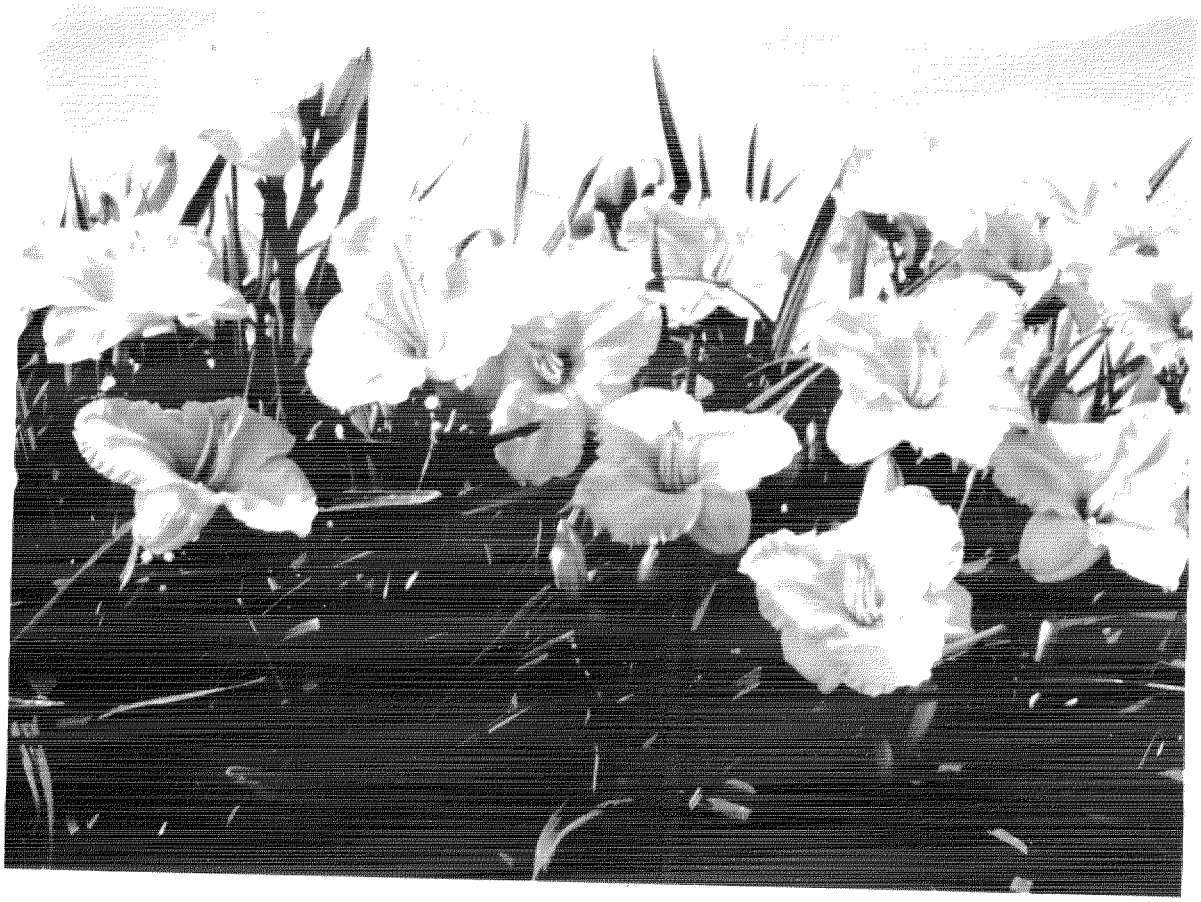
FIG. 1 shows the new hybrid daylily cultivar, which depicts a face view of the flower of the new variety as well as some of the foliage to illustrate its character.

The following is a detailed description of my hybrid daylily cultivar based upon observation of plants grown at Grain Valley, Mo., during 1990–1996; the color designations of the flower are based on the PMS Color Chart.

The Plant

Origin: It should be noted that the plant was initially selected from a daylily planting being grown near Grain Valley, Mo. in a cultivated area and has since been reproduced by vegetative division in the vicinity of Grain Valley, Mo., with the new and distinct characteristics stated herein, found to be maintained through successive generations as before recited.

Parentage:

*Pod parent.*—'Martha Adams' (unpatented).

*Pollen patent.*—Pink Roberson Seedling No. RJR-PK3-89.

Classification:

*Botanic.*—Hemerocallis hybrid

*Commercial.*—Daylily cultivar 'Robgloper'.

Form: Single stem, erect and stately scape from a fan shaped plant made up of narrow arching grass-like, long keeled glabrous leaves 2-ranked at the base of the scape.

Foliage:

*Quantity.*—Abundant, a mature plant having about 12 leaves.

*Leaf size.*—About 1½" wide and about 15" long.

*Leaf shape.*—Linear and long keeled with entire margins.

*Texture.*—Glabrous.

*Color.*—Dark Green (PMS#349).

Scape:

*Color.*—Medium Green (PMS#357).

*Height.*—About 20"–22".

The Bud

Form: Modified oblanceolate.

Size (day before opening):

*Length.*—About 5.1 cm.

*Width.*—About 2 cm.

Opening rate: About 6 hours.

Color:

*When sepals first divide.*—Pale-Buff-Melon (PMS#148).

Penduncle:

*Character.*—Rigid and sturdy.

*Color.*—Dark Green (PMS#364).

The Flower

Blooming habit: Flowers begin to appear on the established plant in mid-season or the middle of the hemerocallis blooming season which is referred to as "peak bloom". 'Robgloper' blooms an average of 28 days to 110 days depending on the USDA zone.

lower size:

*Diameter.*—About 5½".

*Depth.*—About 2".

hape: Side, round, ruffled, overlapping.

orne: Singly on the branchlets of a sturdy, erect rachis which is ramulous; each scape has at least four or five peduncles which divides into twelve or fifteen pedicels.

umber of blooms per scape: 12–15.

etalage: The flower consists of six perianth segments (i.e. tepals) consisting of three sepals (the outer segments) and three petals (the inner segments) all in an imbricated arrangement.

The Sepals hape: Oblanceolate with slightly undulated entire margins and an acuminate apex.

ize: About 3" long and 2" wide.

exture: Diamond dusted & slightly ribbed.

olor: Peach (PMS#162).

The Petals hape: Broadly obovate with entire undulated margins and a broadly cuspidate apex.

olor: Clear peach (PMS#162) with very faint rose (PMS#169) halo on cool, wet mornings. The basal portion of the petals (throat) exhibit a faint lemon-yellow (PMS #100) coloration which surrounds a lime-green (PMS #387) "heart" (deepest portion at center of flower).

exture: Heavy, thick, slightly ribbed.

ize: About 3" wide; 3½" long.

ffect of weather: Very resistant to sun and rain; substance and color holds well.

ragrance: Slightly sweet floral scent.

isease resistance: This cultivar, as most hemerocallis, has not been noted to be very susceptible.

Lasting quality: Excellent lasting quality due to tepals having thick heavy, spongy consistency which aids in fresh and turged blooms throughout the day.

The Reproductive Organs

Stamens:

*Number.*—Six to eight.

*Arrangements.*—Inserted individually at the summit of the perianth tube.

*Anthers.*—Arrangement; Introse. Size — 5 mm. Color — Brown (PMS#438)

*Filaments.*—Slender and 4 cm in length. Color — Pale Gold (PMS #127).

*Pollen.*—Color — Gold (PMS#123).

Pistils:

*Number.*—One.

*Style.*—Length — 7 cm. Color — Pale Gold (PMS#127).

*Stigma.*—Color — White & glistening.

*Character of ovaries.*—Three celled.

*Shape.*—Oblong, becoming a loculieidally 3 — valved capsule.

The Fruit (Seed Pod)

Shape: The seed pod is an ovoid capsule.

Measurements: 1¼ inch length and 1⅙ inch width.

Color: Ranges from pale green (PMS#372) to Olive Brown (PMS#140) at maturity.

Fertility: A Yes, it is fertile.

GENERAL OBSERVATIONS

'Robgloper', with its clear peach blooms, having heavy substance and fragrance, its strong short scapes, and repeat blooming habit, is an improved Hemerocallis cultivar in the pink-peach color category, and should help meet the need for good landscape performing daylilies.

I claim:

1. The new and distinct variety of daylily plant as substantially illustrated and described.

* * * * *